(12) United States Patent
Kayser

(10) Patent No.: US 10,215,719 B2
(45) Date of Patent: Feb. 26, 2019

(54) SECONDARY ION MASS SPECTROSCOPIC METHOD, MASS SPECTROMETER AND USES THEREOF

(71) Applicant: ION-TOF TECHNOLOGIES GMBH, Muenster (DE)

(72) Inventor: Sven Kayser, Muenster (DE)

(73) Assignee: ION-TOF TECHNOLOGIES GmbH, Muenster (DE)

(*) Notice: Subject to any disclaimer, the term of this patent is extended or adjusted under 35 U.S.C. 154(b) by 0 days.

(21) Appl. No.: 15/692,077

(22) Filed: Aug. 31, 2017

(65) Prior Publication Data

US 2018/0067062 A1    Mar. 8, 2018

(30) Foreign Application Priority Data

Sep. 2, 2016 (EP) .................................... 16186930

(51) Int. Cl.
| | |
|---|---|
| *H01J 49/40* | (2006.01) |
| *H01J 49/00* | (2006.01) |
| *G01N 23/2258* | (2018.01) |
| *H01J 49/14* | (2006.01) |

(52) U.S. Cl.
CPC ........ *G01N 23/2258* (2013.01); *H01J 49/142* (2013.01); *H01J 49/40* (2013.01); *G01N 2223/611* (2013.01); *G01N 2223/652* (2013.01); *H01J 2203/04* (2013.01)

(58) Field of Classification Search
CPC .......... H01J 49/142; H01J 49/10; H01J 37/08; H01J 37/305; H01J 27/26; H01J 2237/0041; H01J 2237/0812; G01N 23/00; G01N 23/22; G01N 23/225

USPC ... 250/281, 282, 287, 283, 288, 424, 423 R, 250/492.3

See application file for complete search history.

(56) References Cited

U.S. PATENT DOCUMENTS

| | | | |
|---|---|---|---|
| 9,378,937 B2* | 6/2016 | Kollmer | H01J 27/26 |
| 9,861,588 B2* | 1/2018 | Sanchez Barreiro | A61K 9/5123 |
| 2013/0092831 A1* | 4/2013 | Kyogaku | H01J 49/0004 250/282 |
| 2013/0153892 A1* | 6/2013 | Sasaki | H01L 29/66969 257/43 |

(Continued)

OTHER PUBLICATIONS

Wang Zhaoyi Ng et al: "Argon Cluster Sputtering Source for ToF-SIMS Depth Profiling of Insulating Materials: High Sputter Rate and Accurate Interfacial Information", Journal of the American Society for Mass Spectrometry, Elsevier Science Inc, US, Bd. 26, Nr . 8, May 8, 2015 (May 8, 2015), pp. 1283-1290.

(Continued)

*Primary Examiner* — David A Vanore
(74) *Attorney, Agent, or Firm* — Robert W. Morris; Eckert Seamans Cherin & Mellott, LLC

(57) ABSTRACT

In a secondary ion mass spectroscopic (SIMS) method, and a mass spectrometer for implementing the method, for depth-profiling analysis of alkali metals in a sample which comprises an insulating material or is an insulator. The sample is irradiated by an ion beam as an analysis beam for desorption of secondary ions from the uppermost layers, such that the surface of the sample is removed with the same or a further ion beam. The ion beam used for removal of the sample surface comprises essentially gas clusters or consists of gas clusters.

18 Claims, 5 Drawing Sheets

(56) References Cited

U.S. PATENT DOCUMENTS

| | | | |
|---|---|---|---|
| 2013/0213933 A1* | 8/2013 | Kirkpatrick | H01J 37/08 216/60 |
| 2013/0277549 A1 | 10/2013 | Kimura et al. | |
| 2014/0252225 A1 | 9/2014 | Iwasaki | |
| 2014/0332679 A1 | 11/2014 | Blenkinsopp et al. | |
| 2014/0374585 A1* | 12/2014 | Murayama | G01N 23/2258 250/282 |
| 2014/0374587 A1* | 12/2014 | Murayama | H01J 49/10 250/282 |
| 2015/0311057 A1* | 10/2015 | Murayama | G01N 23/2258 250/282 |
| 2018/0025897 A1* | 1/2018 | Reed | H01J 49/142 |

OTHER PUBLICATIONS

Fujimoto Hiroshi et al : "Origin of 1,4-8,H external quantum efficiency degradation in organic light-emitting diodes with a DC magnetron sputtered cathode", Journal of Vacuum Science & Technology B: Microelectronics and Nanometer Structures, American Institute of Physics, 2 Huntington Quad Rangle, Melville, NY 11747, Bd. 32, Nr . 6, Oct. 15, 2014 (Oct. 15, 2014).

Ninomiyas et al: "Secondary ion measurements for oxygen cluster ion SIMS", Applied Surface Science, Elsevier, Amsterdam, NL, Bd. 252, Nr. 19, Jul. 30, 2006 (Jul. 30, 2006), pp. 7290-7292.

European Search Report of Corresponding EP Application No. 16 186 930.0.

\* cited by examiner

SECONDARY ION MASS SPECTROSCOPIC METHOD, MASS SPECTROMETER AND USES THEREOF

BACKGROUND OF THE INVENTION

The present invention relates to a secondary ion mass spectroscopic method (SIMS) and also a mass spectrometer for implementing this method. Furthermore, the present invention relates to a use of such a method or of such a mass spectrometer for examining alkali metals in a sample which comprises an insulating material or is an insulator.

In microelectronics, mobile ions, such as e.g. sodium and potassium, play a very important role. If these are present as impurities in electronic components, then they can diffuse very rapidly into the dielectric layers as a result of the applied voltages. Such impurities can then significantly impair the properties of a component. Therefore, in order to optimise the reliability and lifespan of an electronic component, a sensitive and quantitative detection method for alkali metals is required. Also the properties of glasses are greatly influenced by alkali metals. Great significance is attributed to alkali metals, such as e.g. sodium and potassium, in glass corrosion.

Secondary ion mass spectrometry (SIMS) is an established method for determining the depth distribution of elements and compounds in thin layers. The surface is thereby bombarded with primary ions of a few keV energy and the emitted secondary ions are analysed with a mass spectrometer. By scanning a focused primary ion beam, a uniform removal on a surface to be analysed can be achieved. Thus the secondary ion intensities can be determined as a function of the sputtered depth. SIMS is distinguished by particularly low detection limits in ppm into the ppb range. The thus obtained intensity profiles (intensity versus measuring time) can be calibrated correspondingly by suitable measurements of the removal depth and can be converted into depth profiles.

The secondary ion yield (defined as number of emitted secondary ions per primary ion) for a chemical element depends very greatly upon the chemical environment. This can be exploited by using primary ions which are reactive for the removal. By implanting these primary ions, the chemistry of the surface is changed such that an increased secondary ion yield is achieved. It is known that, by using oxygen primary ions ($O_2^+$), the emission of positive secondary ions is enhanced. This is generally used for sensitive detection of electropositive elements, such as metals and alkali metals. The secondary ion yield of electronegative elements is enhanced by implanting caesium. Both types of primary ions are used routinely in SIMS.

Analysis of the emitted secondary ions can be effected with various mass spectrometers. Magnetic sector field devices or quadrupole mass spectrometers are established for depth profiling. Generally, the mass spectrometer is operated here as a mass filter. The intensity of the various secondary ion masses can be determined by the corresponding change in mass filter. These types of mass spectrometers operate with continuous primary ion beams.

Furthermore, also time-of-flight mass spectrometers (ToF) are widespread in SIMS. In the case of the method termed ToF-SIMS, the surface is bombarded with a short ion pulse. The desorbed secondary ions are accelerated and their flight time is measured over a suitable flight path. From this flight time, the mass of the secondary ions can be determined. With this type of spectrometer, all secondary ion masses, which are produced by a primary ion pulse, can be determined via measurement of the flight time. Therefore a parallel recording of all masses takes place. Since however the removal rate is reduced by the pulsing of the primary ion beam by several orders of magnitude, the dual-beam method is used predominantly for depth profiling. After bombardment by the primary ion pulse, the sample surface is sputtered with a second sputter ion source during the flight time measurement. In order to increase the secondary ion yield, typically oxygen- and caesium ion sources are used here as sputter ion source. As analysis source, so-called liquid metal ion sources have been successful. Examples of these are gallium-, gold- and bismuth liquid metal ion sources.

Bombardment by electrically charged primary ions and also the emission of charged secondary particles, such as electrons, positive or negative charged secondary ions, leads to a change in the surface potential in the case of insulating samples. As a result of the effect of the electrically charged region on the desorbed secondary ions, this can lead not only to a change in the energies thereof but also to a change in the trajectories thereof. Both can result in significant transmission losses in the mass spectrometer. Furthermore, this frequently also causes a significant impairment in the mass resolution. Due to the charging of the sample surface in conjunction with the primary ion bombardment, the result can also be changes in the sample. It is known that some elements can move in the sample (electromigration) under the effect of the charge. In particular alkali metals are inclined to do this. As a consequence of the charge, the intensity- or depth distributions are often very greatly falsified.

For compensation of the charges, very frequently electron beams are used. Charging of the sample surface by the primary ion beam, in the dual-beam method also by the sputter ion beam, is generally electrically positive. The negative charging of the electrons is then intended to compensate precisely for the positive charges. This can be effected by corresponding control of the current densities of the ion- and electron beams. By using an excess of very low-energy electrons with an energy of a few eV, also automatic stabilisation of the surface potential can be achieved. The surface absorbs electrons only until the surface potential corresponds to the potential of the electron source (potential of the emitting cathode of the electron source). This method is used frequently in ToF-SIMS. Here the extraction field for the secondary ions can be switched off during the flight time measurement. Thus the low-energy electrons can reach the analysis location and compensate for the charging.

Use of these charge compensation methods allows extensively reliable measurement of the secondary ion intensities. However also electromigration frequently takes place even with a significantly reduced charging of the sample. As a result of the residual low charge, some elements can be removed from the surface and thus are no longer available for desorption by the primary ion beam. This problem is particularly pronounced during depth profiling of alkali metals in insulators, such as e.g. $SiO_2$ and glasses. Shortly after the beginning of the depth profile, the intensity of the alkali ions collapses very greatly. Only upon reaching a conductive layer below the insulating layer is the electromigration stopped. This leads to excessive concentrations and secondary ion intensities at the interface.

Depth profiling of insulators by means of SIMS is significantly complicated by charges on the sample surface. Even using electrons for charge compensation results in electromigration of some elements, such as e.g. alkali metals. If $O_2^+$ primary ions are used to increase the positive secondary ion yield, then this electromigration is particularly pronounced and prevents measurement of the correct depth distribution.

It has been shown in practice that the electromigration can be significantly reduced by the use of caesium ion sources. However, the positive ion yield is significantly reduced. The result of this is considerable impairment in the detection limits.

SUMMARY OF THE INVENTION

It is therefore the object of the present invention to make available a secondary ion mass spectroscopic method and a mass spectrometer suitable for this purpose, with which depth profiling of insulating materials, in particular on alkali metals contained therein, is possible with as low as possible or no falsification of the depth distribution with simultaneously low detection limits. Furthermore, it is the object of the present invention to make available uses for such methods or mass spectrometers.

This object is achieved by a secondary ion mass spectroscopic method, and a mass spectrometer, wherein the ion beam used for removal of the sample surface essentially comprises or consists of gas clusters.

More particularly, the secondary ion mass spectroscopic method according to the invention for depth profiling of alkali metals in a sample which comprises an insulating material or is an insulator is implemented as single- or dual-beam SIMS. This means that, as sputter ion beam for removal of surface-proximal layers and for analysis of surface-proximal layers with desorption of secondary ions to be analysed, either the same ion beam or two different ion beams can be used.

According to the invention, at least the ion beam used for removal of the sample surface (sputtering) comprises predominantly or substantially gas clusters which can be preferably gas clusters of oxygen molecules and/or of oxygen-containing molecules. The proportion of such gas clusters is advantageously greater than or equal to 40%, advantageously up to 90% of clusters, which comprise oxygen molecules and/or oxygen-containing molecules or consist completely thereof.

It is possible to use the same beam also as analysis beam or for example to use other primary ions for the analysis beam, such as for example bismuth or the like.

In order to produce gas clusters made of oxygen molecules and/or oxygen-containing molecules, a so-called gas cluster ion source (GCIS) can be used particularly advantageously. In the case of the latter, a gas/gas mixture which comprises $O_2$ molecules or consists thereof is expanded in a vacuum chamber by means of a nozzle with a pressure of several bar. Gas clusters of oxygen molecules and/or oxygen-containing molecules are hereby formed.

The thus-formed gas clusters can be ionised by means of an electron beam or in another way and then subsequently accelerated. They then serve, according to the invention, for sputtering the surface of the sample and/or also additionally for analysis of the sample surface.

Experimental tests relating to electromigration on insulators have shown that in particular oxygen gas cluster ions with energies of a few keV to some 10 keV are suitable for depth profiling on insulators. These oxygen gas clusters are produced in a vacuum chamber by expansion of an $O_2$ gas or a gas mixture from a gas nozzle at pressures of several bar. After ionisation of these gas clusters, e.g. by means of an electron beam, these can be accelerated and used as ion source for sputtering or for analysis in SIMS. The ion beams comprise gas clusters with a wide size distribution of a few 100 to a few 1,000 molecules. The centre of the size distribution is typically at 500 to 2,000 molecules per ion.

In the case of energies of typically 3 keV to 50 keV, advantageously 10 to 20 keV, sufficiently high sputtering yields can be achieved for removal of inorganic samples. Bombardment of the surface with these gas cluster ions leads to oxidation of the sample surface. This oxidation enhances the emission of positive secondary ions and consequently allows particularly low detection limits to be achieved. It could be shown that the electromigration can be completely prevented under these sputtering conditions. Thus, by the use of oxygen gas cluster ions, a depth profiling on insulators can be implemented without disturbing the depth distribution by electromigration.

In summary, it can be established that, according to the invention, the removal of the sample surface for the depth profiling is effected by means of an ion beam which comprises predominantly or substantially gas clusters of oxygen molecules and/or oxygen-containing molecules. As a result, a depth profiling also of samples comprising insulators or insulating material is possible on alkali metals, in the case of which, on the one hand, a low detection limit is possible and, on the other hand, falsifications of the depth distribution are avoided.

Examples of methods and mass spectrometers according to the invention are subsequently given.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
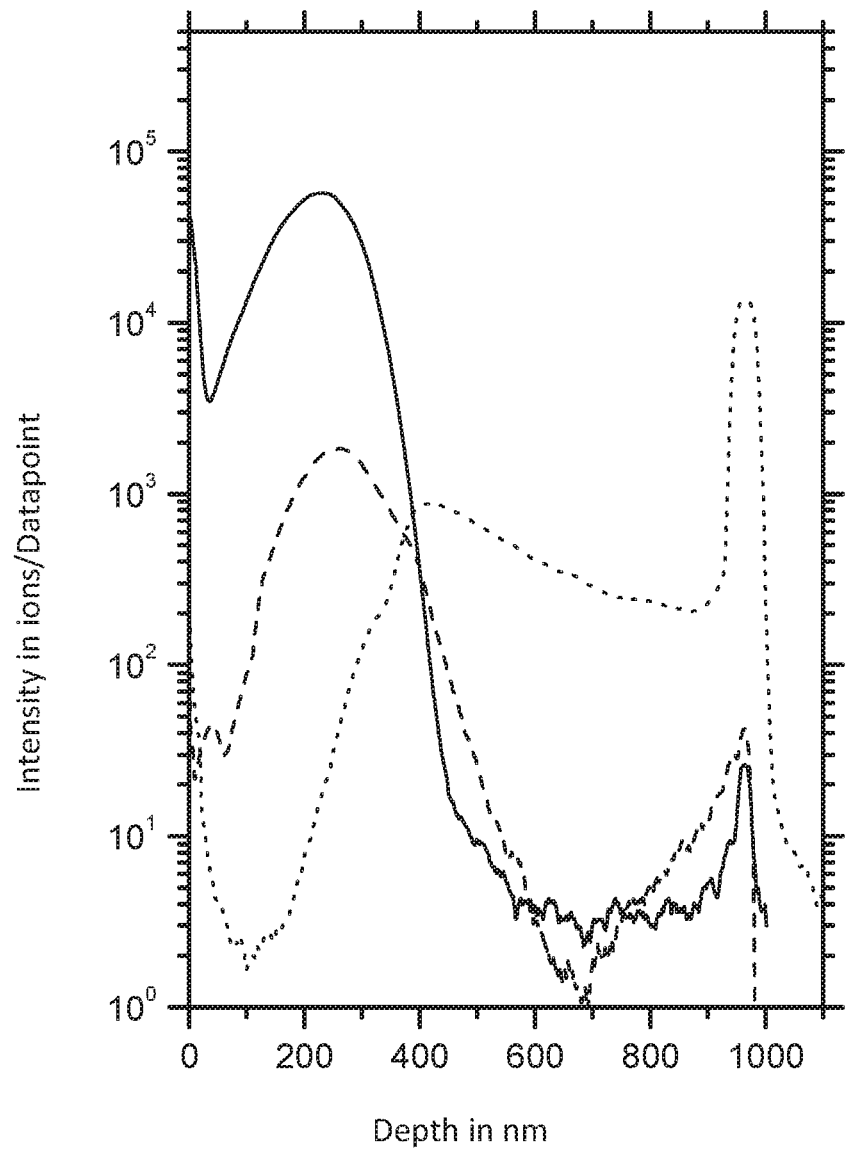
FIG. 1 shows a measurement of the $Na^+$ secondary ion intensity as a function of the depth by means of ToF-SIMS on an approx. 1 µm thick $SiO_2$ layer on a silicon substrate with a removal with $O_2$, Cs and $O_2$ gas clusters.

The preferred embodiments of the present invention will now be described with reference to FIGS. 1-5 of the drawings. Identical elements in the various figures are designated with the same reference numerals.

FIG. 1 shows a depth profile recorded by a ToF-SIMS device. The $Na^+$ secondary ion intensity as a function of the removed depth is illustrated. It concerns a logarithmic intensity scale in which the number of recorded secondary ions per data point is indicated. As sample, an approx. 1 µm thick $SiO_2$ layer which is applied on a silicon substrate was used. In this 1 µm thick $SiO_2$ layer, sodium with an energy of 120 keV with a surface dose of $5 \cdot 10^{14}$ ions/cm² had been implanted. The depth distribution of such an implantation profile is basically known. The present measurement serves for demonstrating the excellent properties of oxygen gas cluster ions as sputter ions relative to a conventional depth profiling by means of oxygen ions $O_2^+$ or caesium ions $Cs^+$.

In a first measurement, the sample was analysed in a ToF-SIMS mass spectrometer "ToF.SIMS 5" of ION-TOF GmbH with a dual-beam method using oxygen ions $O_2^+$. A bismuth liquid metal ion source with the primary ion species $Bi_1^+$, an energy of 30 keV and an analysis surface of 100×100 µm$^2$ served as pulsed analysis beam. The analysis current was 4.6 pA at a pulse frequency of 10 kHz. The measuring time per data point was 1.6 s. The removal was effected on a surface of 300×300 µm$^2$ with an $O_2^+$ ion beam with an energy of 2 keV and an ion current of 255 nA. As is common in the state of the art, a low energy electron source with an electron energy of 20 eV was used for compensation of the surface charge by the oxygen ion beam. The associated measurement is illustrated in FIG. 1 as a dotted curve.

As was to be expected, the measured depth profile (dotted curve) is extremely distorted by electromigration. Shortly after the beginning of the depth profile, the sodium intensity falls to extremely low values. Only after some time of the depth profiling, i.e. apparent at a greater depth, does the intensity then increase again slightly. At the interface between the $SiO_2$ layer and the silicon substrate, the signal then increases extremely sharply and then falls again rapidly in the silicon to very low values. Therefore a typical signal progression for electromigration is produced since the sodium atoms react to the surface charge and move away from the surface. Only when reaching the interface does the electrical conductivity of the sample increase again and the surface charge and hence also the electromigration disappears. The sodium signal hence increases again greatly and the result is an excess of sodium signals because of accumulation of migrated sodium ions in this zone of the sample. The depth distribution was therefore very greatly falsified by this measurement.

In the case of a second measurement which is illustrated by a broken-lined curve in FIG. 1, a caesium ion beam was used, with identical analysis conditions, for the sputtering of the sample surface between the individual analyses. The energy of the ion beam was 2 keV with a beam current of 145 nA. As was to be expected, the electromigration is significantly reduced. The sodium intensity profile corresponds approximately to the expected depth distribution which occurs on insulators, such as $SiO_2$, with implanted sodium ions. Nevertheless slight electromigration takes place and leads to a small excess of the signal at the interface to the silicon substrate. However, a serious disadvantage of this method is the low sensitivity of the measurement. By introducing caesium, the positive secondary ion yields which are essential for sodium are significantly reduced. At the maximum of the distribution, the intensity is below 2,000 ions/data point.

Figure 3:
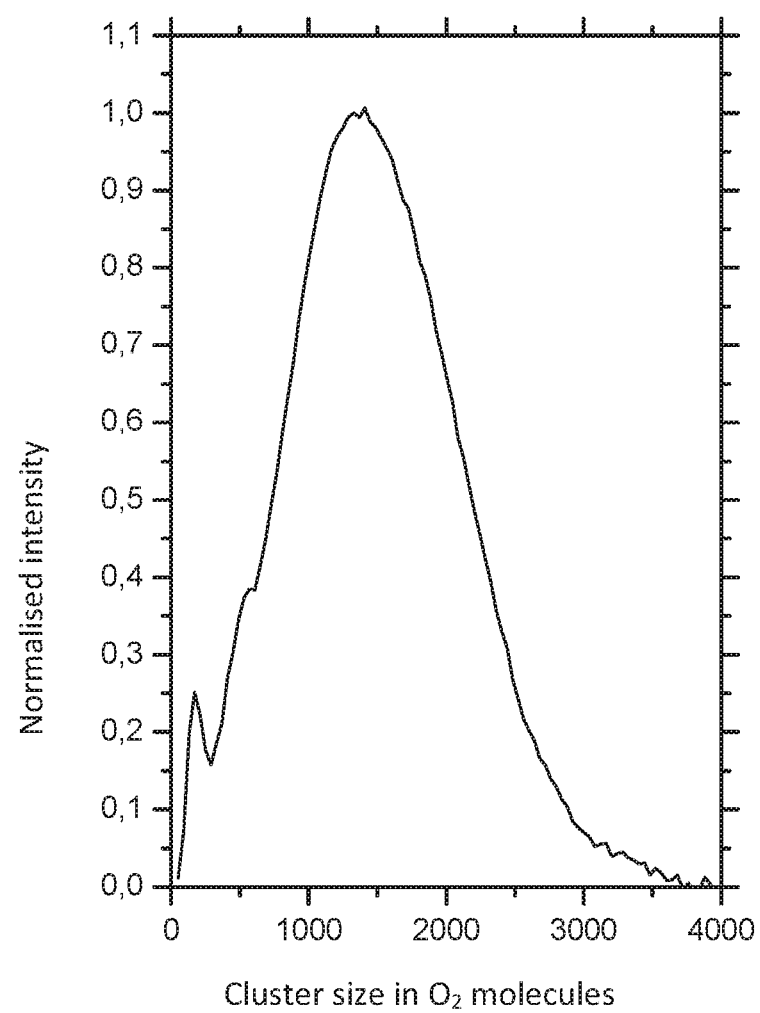
FIG. 3 shows the cluster size distribution in an oxygen gas cluster ion beam.

The continuous line in FIG. 1 was measured with a method according to the invention and a mass spectrometer equipped according to the invention. For the removal of surface layers, large oxygen gas clusters with essentially 1,400 molecules/ion and an energy of 20 keV were used for depth profiling with the same analysis parameters. The oxygen gas clusters were produced by a nozzle with an inlet pressure of approx. 35 bar. The gas cluster beam propagating in the vacuum was ionised with an electron beam and subsequently accelerated to 20 keV beam energy. The typical size distribution of the oxygen gas cluster ions is illustrated in FIG. 3. The size distribution is very wide and begins at approx. 100 $O_2$ molecules and reaches up to approx. 3,800 $O_2$ molecules. The maximum is at 1,400 $O_2$ molecules per cluster ion. For the removal, the gas cluster beam was scanned over a surface of 300×300 µm$^2$ with a beam current of 4.9 nA.

The continuous line in FIG. 1 corresponds precisely to the implantation profile which is to be expected and known. In particular on the curve progression at the interface between the $SiO_2$ insulator layer and the silicon substrate at a depth of 1,000 nm, the extremely low electromigration occurring with this measuring method is shown. The intensity at this interface is below the highest intensity in the depth profile by approx. three orders of magnitude.

It should be assumed as operating mechanism that, by the use of the oxygen gas clusters as sputter ions, the surface of the sample is very well oxidised, which leads to a significantly increased positive secondary ion yield for sodium during desorption by the Bi analysis beam. Consequently, very low detection limits for sodium in the insulating material result therefrom. The minimum concentration which can be detected is below the peak concentration of the implantation profile by more than four orders of magnitude. The special interaction between cluster projectile and surface in conjunction with a higher sputter yield lead to almost complete elimination of the electromigration of alkali metals in the insulators.

Figure 2:
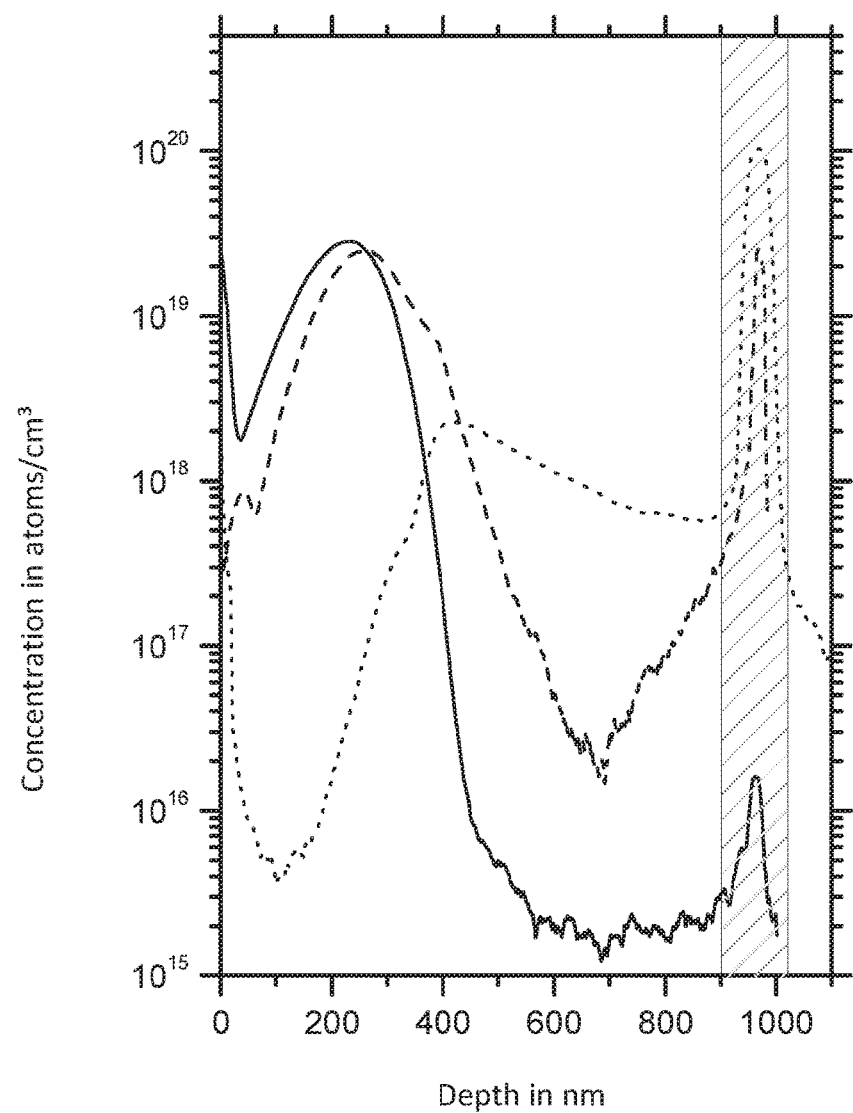
FIG. 2 shows a measurement of the Na concentration as a function of the depth by means of ToF-SIMS on an approx. 1 µm thick $SiO_2$ layer on a silicon substrate with a removal with $O_2$, Cs and $O_2$ gas clusters.

FIG. 2 shows the measuring results of FIG. 1 with the three different sputter ion beams after a calibration to the implantation dose on a logarithmic concentration scale in atoms/cm$^3$. Whilst the peak concentration in the measurement with oxygen gas clusters is determined at $3 \cdot 10^{19}$ atoms/cm$^3$ (continuous line), the electromigration with the $O_2$ sputter beam (dotted line) leads to completely false results. At the maximum of the implantation profile, a concentration reduced by more than 2 orders of magnitude is measured and, at the interface to the silicon substrate, the concentration increases to approx. $10^{20}$ atoms/cm$^3$. The concentration profile under caesium sputter removal (broken-line) shows a merely slightly lower peak concentration in comparison with the oxygen gas cluster ions. However, as a result of the electromigration, the concentration at the interface is still above $2 \cdot 10^{19}$ atoms/cm$^3$. Reduction in the ion yield leads to a poorer detection limit of approx. $2 \cdot 10^{16}$ atoms/cm$^3$, whilst, with $O_2$ gas cluster ions, detection limits below $2 \cdot 10^{15}$ atoms/cm$^3$ are achieved.

As a measure for the strength of the electromigration, the proportion of the Na dose in the $SiO_2/Si$ interface can be determined. The proportion of the dose in the hatched region in FIG. 2 was determined for all three removal conditions:

| a. | $O_2$ sputter ion beam (dotted curve) | 94% |
| b. | Cs sputter ion beam (broken-line curve) | 9.2% |
| c. | $O_2$ gas cluster ion beam (continuous curve) | 0.01% |

It becomes very clear herefrom that the electromigration under oxygen gas cluster removal is practically negligible and the concentration profile can be determined quantitatively.

Figure 4:
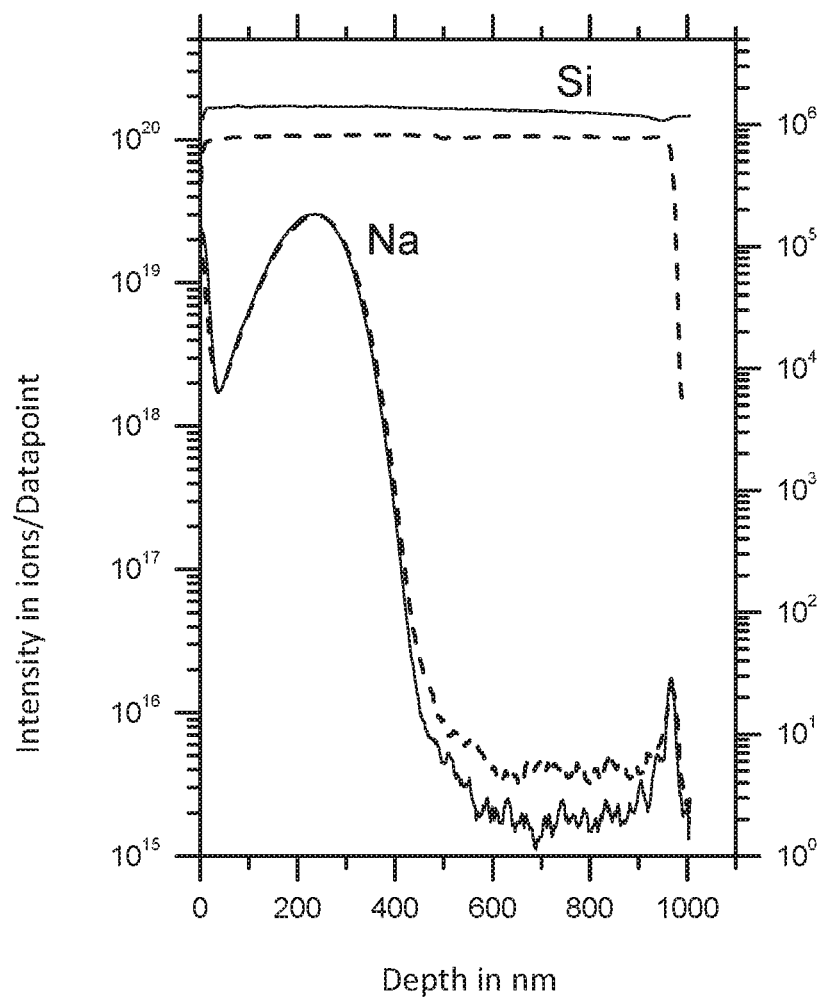
FIG. 4 shows a measurement of the $Na^+$ secondary ion intensity as a function of the depth by means of ToF-SIMS on an approx. 1 µm thick $SiO_2$ layer on a silicon substrate for oxygen- and argon gas cluster removal.

In FIG. 4, the depth profile with removal by oxygen gas clusters (see FIG. 1) is compared with the removal by an argon gas cluster beam. The analysis- and sputtering parameters are the same for both measurements. FIG. 4 shows the depth profile for the silicon matrix signal $Si^+$ and also for $Na^+$ for both different gas cluster beams. The oxygen gas cluster beam obtains complete oxidation of the $SiO_2$ during removal and also leads to complete oxidation of the silicon substrate. This is shown on the Si$^+$ profile under oxygen gas cluster bombardment (continuous line). Under argon gas cluster bombardment (broken-line), the oxidation is slightly reduced and the signal intensity of the Si$^+$ is slightly lowered. In the silicon substrate, the signal then breaks down greatly since, because of the lack of oxygen, the positive ion yield is reduced by several orders of magnitude. The Na$^+$ profile under both bombardment conditions is very similar. The detection limits under oxygen gas cluster removal are lower approximately by a factor 2.5. This example shows that the alkali concentrations in the SiO$_2$ can be determined correctly with both types of gas cluster beams. The concentration profile in the silicon substrate can however be measured only with the oxygen gas cluster beam since the latter ensures complete oxidation and hence constant ionisation.

Figure 5:
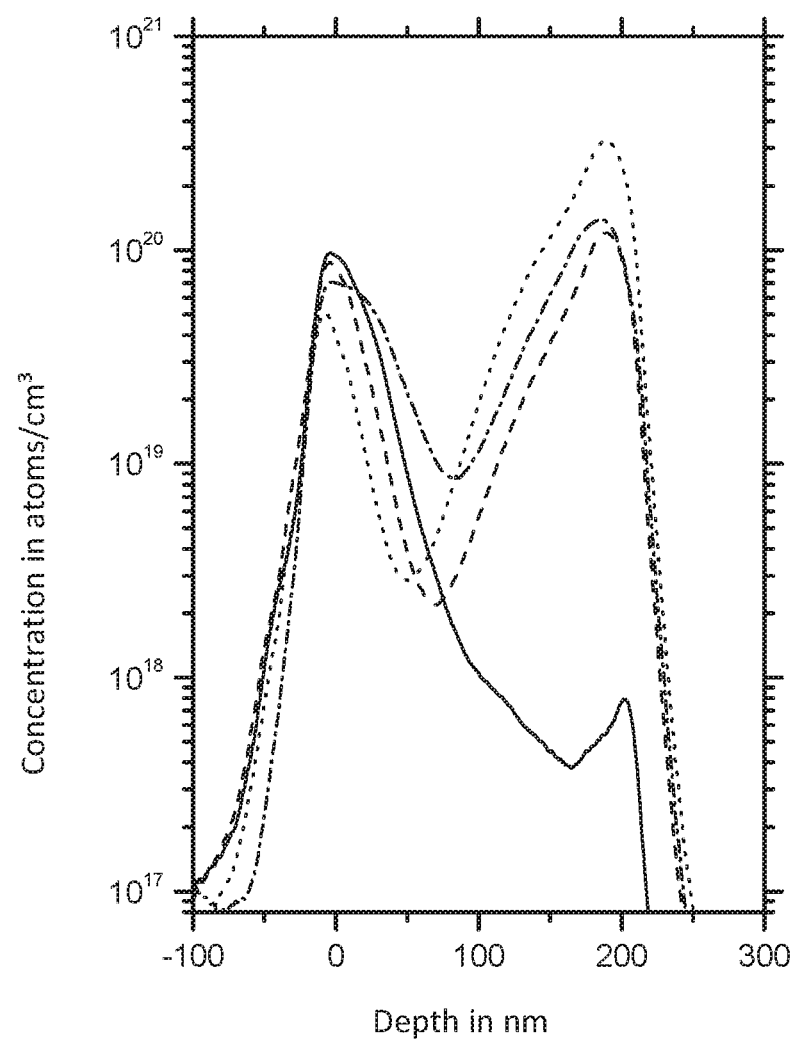
FIG. 5 shows measurements of the Na concentration profile for differently treated $SiO_2$ samples.

FIG. 5 shows further depth profiles which were measured on different SiO$_2$ layers. In microelectronics, the mobile ions, such as e.g. sodium and potassium, play a very important role since they rapidly diffuse as impurities in components due to the applied voltages in the dielectric layers and as a result the properties of a component can be considerably impaired. Therefore for optimisation of the reliability and lifespan of a component, a sensitive and quantitative detection method for alkali metals is required. The SiO$_2$ insulator layers in the test samples used have a thickness of 200 nm and are applied respectively on a silicon substrate. In the case of these samples, sodium was introduced specifically by electromigration into the SiO$_2$ insulator layer. The samples differ by the length and the direction of the migration process. Thereafter, the samples were coated with gold. The thickness of the coating is approx. 40 nm. The curves illustrated in FIG. 5 show the sodium distribution in the individual samples. The measurements were effected in the dual-beamdual-beam method. A bismuth-liquid metal ion source with the primary ion species Bi$_1^+$, an energy of 30 keV and analysis surface of 100×100 μm$^2$ served as pulsed analysis beam. For removal of the surface layers for depth profiling, large oxygen gas clusters with essentially 1,400 molecules/ion and an energy of 20 keV were used according to the invention. The removal was effected on a surface of 300×300 μm$^2$.

The dash/dot curve shows the distribution of the sodium ions after introduction of sodium into the SiO$_2$ layer was approx. half-finished. The dotted curve represents the sodium distribution after complete conclusion of the migration. The broken-line curve shows distribution after half of the migration in the reverse direction. The continuous curve shows the sodium distribution after the sodium had been removed again from the layer. The results show that the method according to the invention enables quantitative analysis of these samples.

There has thus been shown and described a novel secondary ion mass spectroscopic method, mass spectrometer and uses thereof which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a secondary ion mass spectroscopic (SIMS) method for depth-profiling analysis of alkali metals in a sample comprising an insulating material, the sample being irradiated by an ion beam as an analysis beam for desorption of secondary ions from the uppermost layers of the sample and the surface of the sample being removed with the same or a further ion beam,
   the improvement wherein the ion beam used for removal of the sample surface essentially comprises or consists of gas clusters, and wherein the sample comprises alkali metals $\geq 10^{16}*1/\text{cm}^3$.

2. The method according to claim 1, wherein the ion beam used for removal of the sample surface essentially comprises or consists of gas clusters of oxygen molecules or oxygen-containing molecules or both oxygen molecules and oxygen-containing molecules.

3. The method according to claim 2, wherein the ion beam used for removal of the sample surface comprises or consists of $\geq 40\%$ of clusters of oxygen molecules or oxygen-containing molecules or both oxygen molecules and oxygen-containing molecules.

4. The method according to claim 2, wherein the ion beam used for removal of the sample surface comprises or consists of $\geq 60\%$ of clusters of oxygen molecules or oxygen-containing molecules or both oxygen molecules and oxygen-containing molecules.

5. The method according to claim 2, wherein the ion beam used for removal of the sample surface comprises or consists of $\geq 80\%$ of clusters of oxygen molecules or oxygen-containing molecules or both oxygen molecules and oxygen-containing molecules.

6. The method according to claim 2, wherein the ion beam used for removal of the sample surface comprises or consists of $\geq 90\%$ of clusters of oxygen molecules or oxygen-containing molecules or both oxygen molecules and oxygen-containing molecules.

7. The method according to claim 1, wherein the gas clusters are $\geq 80\%$ gas clusters with 100 to 5,000 oxygen molecules or oxygen-containing molecules per cluster molecule or both oxygen molecules and oxygen-containing molecules.

8. The method according to claim 7, wherein the gas clusters are $\geq 80\%$ gas clusters with 500 to 2,000 oxygen molecules or oxygen-containing molecules per cluster molecule.

9. The method according to claim 1, wherein the gas clusters of the ion beam used for removal of the sample surface impinge with an energy of between 3 keV and 50 keV, respectively including or excluding the range limits, on the surface of the sample.

10. The method according to claim 9, wherein the gas clusters of the ion beam used for removal of the sample surface impinge with an energy of between 5 keV and 25 keV, respectively including or excluding the range limits, on the surface of the sample.

11. The method according to claim 9, wherein the gas clusters of the ion beam used for removal of the sample surface impinge with an energy of between 10 keV and 20 keV, respectively including or excluding the range limits, on the surface of the sample.

12. The method according to claim 1, further comprising determining the mass to charge ratio of secondary ions by measuring their time of flight over a known distance.

13. A mass spectrometer for carrying out the method according to claim 1, comprising an ion source for producing the gas cluster ion beam used for removal of the sample surface.

14. A mass spectrometer according to claim 13, wherein the sample comprises an insulating material.

15. The method according to claim 1, wherein the sample comprises alkali metals $\geq 1$ ppm.

16. The method according to claim 1, wherein the sample comprises alkali metals $\geq 10^{19} * 1/cm^3$.

17. The method according to claim 1, wherein the sample additionally comprises SiO.

18. The method according to claim 1, wherein the sample comprises a glass.

* * * * *